United States Patent [19]

Wiezer

[11] Patent Number: 4,526,966
[45] Date of Patent: Jul. 2, 1985

[54] POLYALKYLDIAZASPIRODECANE DERIVATIVES

[75] Inventor: Hartmut Wiezer, Lützelburg, Fed. Rep. of Germany

[73] Assignee: Hoechst Aktiengesellschaft, Fed. Rep. of Germany

[21] Appl. No.: 491,609

[22] Filed: May 4, 1983

[30] Foreign Application Priority Data

May 14, 1982 [DE] Fed. Rep. of Germany ....... 3218172

[51] Int. Cl.³ ................. C07D 498/10; C07D 498/20; C07D 211/48
[52] U.S. Cl. ...................................... 546/19; 524/102
[58] Field of Search .......................................... 546/19

[56] References Cited

U.S. PATENT DOCUMENTS 3,364,220  1/1968  Biel et al. ............................ 546/242
4,220,773  9/1980  Wiezer et al. ......................... 546/19

OTHER PUBLICATIONS

Morrison and Boyd, "Organic Chemistry", (3rd Ed.), (1973), pp. 457-458 and 564-565.

Primary Examiner—Robert T. Bond
Attorney, Agent, or Firm—Connolly and Hutz

[57] ABSTRACT

Polyalkyldiazaspirodecanes which are substituted in the 2-position by functional radicals and have the formula

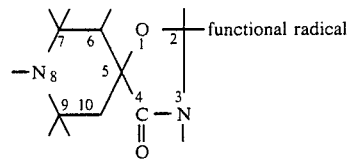

are prepared from polyalkylpiperidine cyanohydrins and ketones which are substituted by functional radicals.

The products are suitable for stabilizing organic polymers against photo-oxidative degradation.

3 Claims, No Drawings

POLYALKYLDIAZASPIRODECANE DERIVATIVES

Numerous polyalkyldiazaspirodecanes which are modified or substituted in a very wide variety of ways are described in the literature (cf., for example, German Patent Nos. 2,606,026, 2,634,957 and 2,834,962). It is a common factor in all these already known compounds that the hydrogen atoms of the $CH_2$ group occupying the 2-position of the oxazolidinone ring can, admittedly, be optionally substituted, but not by alkyl radicals carrying functional groups.

The invention relates, therefore, to new polyalkyldiazaspirodecane derivatives which are substituted in the 2-position of the ring system by an alkyl radical carrying functional groups, to a process for their preparation and to their use as stabilizers for plastics.

The compounds according to the invention correspond to the formula (I)

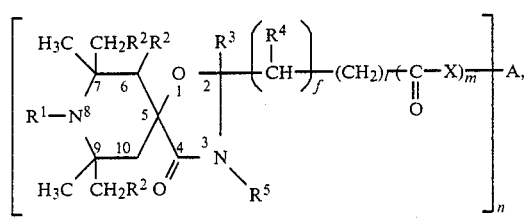

in which $R^1$ is hydrogen, oxygen, $C_1$ to $C_{12}$ alkyl, preferable $C_1$ to $C_4$ alkyl, which can be substituted by 1 OH, or is 2,3-dihydroxypropyl, but particularly is hydrogen, $R^2$ represents hydrogen or $C_1$ to $C_5$ alkyl, preferably hydrogen or methyl and especially hydrogen, $R_3$ denotes a $C_1$ to $C_5$ alkyl group which can be substituted by —COOH, —COOCH$_3$ or —COOC$_2$H$_5$, preferably a $C_1$ or $C_2$ alkyl group, or a phenyl group, and $R^4$ is then hydrogen, or $R^3$ and $R^4$, together with the carbon atoms linking them, form a $C_5$ to $C_{12}$, preferably $C_6$ cycloalkane ring, f is zero or 1, preferably 1, 1 denotes an integer from 0 to 10, preferably from 0 to 7, m represents zero or 1 and n denotes an integer from 1 to 10, preferably 1 to 6 and especially 1 to 4, and is always 1 if m=0, $R^5$ is hydrogen, a $C_1$ to $C_{12}$ alkyl group which can be substituted in the 2-position by OH, or a group of the formula —$(CH_2)_k COOR^6$ in which k is 1 or 2 and $R^6$ represents a $C_1$ to $C_{18}$, preferably $C_1$ or $C_2$, alkyl group, X denotes —O— or

in which $R^7$ has the meanings indicated below for A in the case where m=1 and n=1, and, if m=0 and n=1, A represents a group of the formula (II)

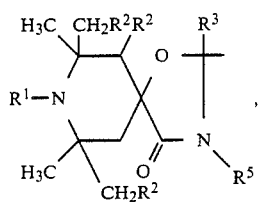

in which $R^1$, $R^2$, $R^3$ and $R^5$ are as indicated above, but in which $R^3$ is not substituted, if m=1 and n=1, A represents hydrogen, $C_1$ to $C_{18}$, preferably $C_1$ to $C_6$, alkyl, $C_3$ to $C_7$ alkenyl, $C_7$ to $C_9$ phenylalkyl, $C_5$ to $C_{12}$ cycloalkyl or 2,2,6,6-tetramethyl-4-piperidinyl, if m=1 and n=2, A represents a $C_2$ to $C_{30}$, preferably $C_2$ to $C_{18}$ and especially $C_2$ to $C_6$, alkylene radical, a $C_4$ to $C_8$ alkenylene radical or a monocycloalkylene, dicycloalkylene or tricycloalkylene radical having 6 to 18, preferably 6 to 12, carbon atoms, if m=1 and n=3, A represents a $C_3$ to $C_8$, preferably $C_3$ to $C_5$, alkanetriyl radical, a radical of the formula

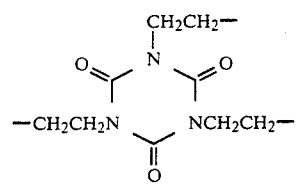

or a group which, together with X, denotes a group of the formula

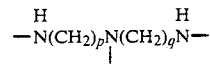

in which p and q are identical or different and represent 2 or 3, if m=1 and n=4, A represents a $C_4$ to $C_8$, preferably $C_5$, alkanetetrayl group or, together with X, represents a group of the formula

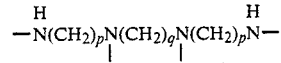

in which p is 2 or 3 and q is 2, and, if m=1 and n>4, A represents a $C_5$ to $C_{10}$ alkane radical which can contain an ether group and is derived from a polyalcohol which does not carry two OH groups per carbon atom, or, together with X, represents a polyethylenepolyamine radical.

The following are examples of compounds falling under the formula (I):
1. Ethyl 2,7,7,9,9-pentamethyl-1-oxa-3,8-diaza-4-oxospiro-[4,5]-decan-2-ylacetate
2. Ethyl 2,7,7,9,9-pentamethyl-1-oxa-3,8-diaza-4-oxospiro-[4,5]-decan-2-ylpropionate
3. Methyl 2,7,7,9,9-pentamethyl-1-oxa-3,8-diaza-4-oxospiro-[4,5]-decan-2-ylbutanecarboxylate
4. Propyl 2,2,4,4-tetramethyl-7-oxa-3,14-diaza-15-oxodispiro-[5.1.5.2]-pentadecan-9-ylpropionate
5. 1,6-Hexane-bis-[(2,7,7,9,9-pentamethyl-1-oxa-3,8-diaza-4-oxospiro-[4,5]-decan-2-yl)-propionamide]
6. 1,6-Hexamethylenedi-[(2,7,7,9,9-pentamethyl-1-oxa-3,8-diaza-4-oxospiro-[4,5]-decan-2-yl)-ethylenylcarboxylate]
7. 1,3,5-Ethylene-2,4,6-trioxo-1,3,5-triazine-tris-[(2,7,7,9,9-pentamethyl-1-oxa-3,8-diaza-4-oxospiro-[4,5]-decan-2-yl)-ethylenylcarboxylate]
8. 1,8-Bis-(7,7,9,9-tetramethyl-2-ethyl-1-oxa-3,8-diaza-4-oxospiro-[4,5]-decan-2-yl)-octane
9. 1,2-Ethylenedioxy-bis-(2,7,7,9,9-pentamethyl-1-oxa-3,8-diaza-4-oxospiro-[4,5]-decan-2-yl)-ethylcarboxylate 10. 2,2,4,4-Tetramethyl-7-oxa-3,14-diaza-15-oxodispiro-[5.1.5.2]-pentadecan-9-ylpropionamide.

The new compounds are obtained, in accordance with the diagram of reactions below, by reacting polyalkylpiperidine cyanohydrins (III) with the equivalent amount to twice the equivalent amount, preferably the amount which is equivalent in respect of keto groups, of a ketone compound of the formula (IV) at 40 to 120, preferably 60 to 100 and especially 70° to 100° C. in a $C_1$ to $C_5$ monocarboxylic acid, preferably acetic acid, as the solvent in the presence of a 1.5-molar to 5-molar, preferably 2.0-molar to 3-molar and especially 2.0-molar to 3.5-molar, amount, relative to the cyanohydrin, of a nonoxidizing inorganic acid, preferably HCl or HBr and especially HCl, and are obtained in the form of a mineral acid salt which is then converted into the free bases (route A).

If it desired to prepare the compounds in which m=1 and n>1, it is preferable to follow a procedure in which compounds (I a) in which X=—O— and A=—CH₃ or —C₂H₅ are first synthesized as described above by route A from (III) and (IV a), and these compounds are then reacted with an equivalent amount of an amine or alcohol of the formula (V) in inert organic solvents and in the presence of 0.1 to 1%, relative to (I a), of a catalyst, such as, for example, LiNH₂, NaH, NaOCH₃ or Ti(O—C₃H₇)₄, with elimination of methanol or ethanol (route B).

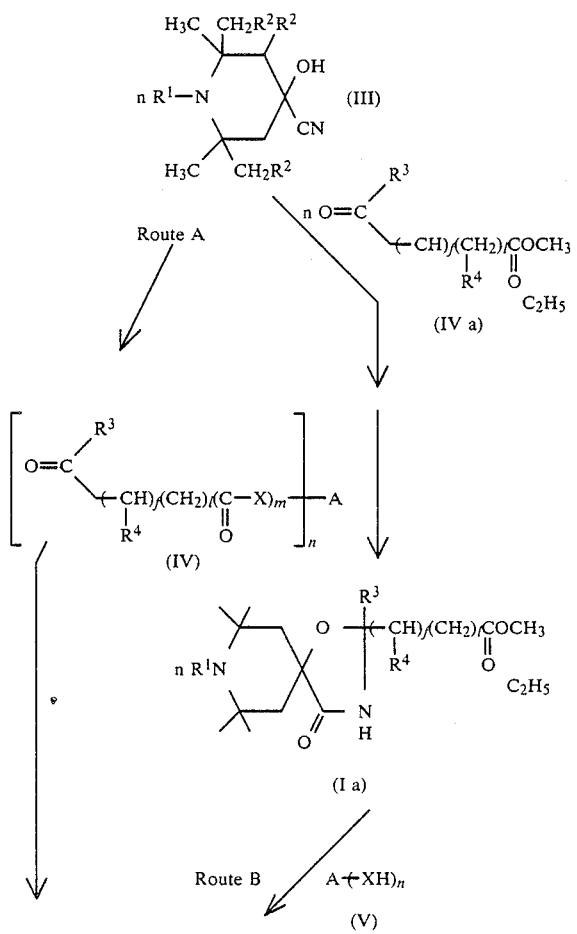

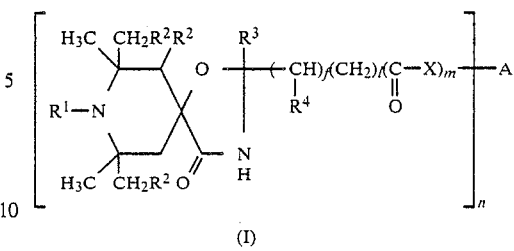

(I)

In the formulae (III), (IV), (IV a), (V), (I) and (I a), $R^1$, $R^2$, $R^3$, $R^4$, f, l, X, m, n and A have the meanings indicated above, A in formula (IV) is a radical

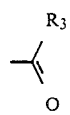

when m=0 and n in formula (IV) preferably represents 1 or 2.

If desired, the compounds (I) or (I a) can then be converted into further derivatives giving products (I) in which $R^5 \neq H$, by reaction with an equivalent amount, relative to the lactam NH of a halogen compound or an epoxide.

The polyalkylpiperidyl cyanohydrins required for the reaction can be prepared, by a method modelled on U.S. Pat. No. 2,295,167, in accordance with the specifications of German Offenlegungsschrift No. 2,830,719. The following may be mentioned as examples of ketone compounds: ethyl levulinate, ethyl pyruvate, ethyl acetoacetate, ethyl 5-oxohexanoate, ethyl cyclohexanone-2-propionate, 3,12-dioxotetradecane and glycol acetoacetate.

It could not have been foreseen that the new compounds could be prepared in the manner described, since it would have been expected that the substituted ketones used as the reactant, particularly in the case of those containing ester groups, would tend to react in or with the acid reaction medium, giving rise to side reactions.

Compared with those of the state of the art, the new compounds are distinguished by a very good effectiveness, combined with a particularly advantageous overall pattern of technical properties in use. A further advantage is that higher molecular weights can be obtained very easily by modifying the functional radical, which is not possible without difficulty in the case of the compounds of the state of the art. It could not have been foreseen, and must be described as surprising, that it would be possible to achieve such advantages by the introduction of a functional radical.

The new polyalkyldiazaspirodecanes which are substituted by functional groups are outstandingly suitable for stabilizing organic polymers, such as are listed, for example, in German Offenlegungsschrift No. 3,045,839 on pages 14 to 19, and it is also possible to add the further additives quoted in this reference. In general, the quantity employed is 0.01 to 5, preferably 0.5 to 2.5 and especially 0.1 to 1, parts by weight, relative to the polymer.

The new compounds are particularly useful for stabilizing polypropylene, polyethylene, polystyrene, ABS resins, poly(meth)acrylates and copolymers of the corresponding monomers; a further preferred field of use for products of the formula (I) in which $R^5$ is not H, is the lacquer sector.

The examples which follow serve to illustrate the invention further.

In the following preparation examples, the process products are characterized by numbers which refer to the numbering of the compounds listed on pages 4 and 5.

EXAMPLE 1 (COMPOUND NO. 2)

500 g of glacial acetic acid, 182 g (1.0 mole) of 2,2,6,6-tetramethylpiperidine-4-hydroxy-4-nitrile and 200 g (1.4 moles) of ethyl levulinate are initially placed in a stirred apparatus, after which 100 g (3 moles) of hydrogen chloride are passed in at approx. 20° C., while cooling. The mixture is stirred for approx. 16 hours at 50° C. while passing a gentle stream of HCl through it. The acetic acid is then removed by vacuum distillation, the residue is taken up in 200 ml of acetone and the precipitated hydrochloride of the desired compound is filtered off with suction. Neutralizing the salt with aqueous ammonia or sodium carbonate solution gives a colorless solid, which is recrystallized from heptane.

Yield: 160 g = 48% of theory; melting point 150° C.

EXAMPLES 2 TO 4

The reaction is carried out as in Example 1 using the same nitrile, and the following are obtained:
- by reaction with ethyl acetoacetate, compound No. 1, melting point 141° C. (Example 2);
- by reaction with propyl cyclohexanone-2-propionate, compound No. 4, melting point 185° C. (Example 3);
- by reaction with 3,12-dioxotetradecane, compound No. 8, melting point 155°–157° C. (Example 4).

EXAMPLE 5 (COMPOUND NO. 5)

13.0 g (0.04 mole) of the compound according to Example 1, 2.3 g (0.02 mole) of hexamethylenediamine and approx. 0.2 g of $LiNH_2$ in 80 ml of absolute mesitylene are stirred at 100° C. in a stirred apparatus, ethanol of the reaction (1.8 g) being removed by distillation. The reaction is complete after 6 hours. The mixture is filtered hot, the filtrate is concentrated to dryness in vacuo and the residue is triturated with ether. The precipitated solid is filtered off with suction.

Yield: 9.0 g, melting point 97° to 99° C.

EXAMPLE 6 (COMPOUND NO. 10)

10 g of the compound according to Example 3 are stirred for 4 hours in 100 ml of concentrated $NH_3$ at 40° C., and the product is filtered off with suction.

Yield: 9 g, melting point 290° C.

EXAMPLE 7

This example shows the volatility of the new stabilizers compared with products of the nearest state of the art.

The volatilities were determined in an apparatus for thermogravimetric analysis. Equal amounts (500 mg) of the compounds according to the invention and of the comparison substances were heated for this purpose in an atmosphere of nitrogen to 300° C. at a rate of heating of 2 K/minute, and the loss of substance in mg/cm² of sample surface was measured. The results are shown in the table below:

| Stabilizer according to Example | Loss of weight in mg/cm² on reaching ...°C. | | | |
|---|---|---|---|---|
|  | 220 | 260 | 300 | 10 minutes at 300 |
| 1 | 3.95 | 15.96 | 71.1 | 107.44 |
| 5 | 0.0 | 0.95 | 7.09 | 12.01 |
| 6 | 0.63 | 2.37 | 12.64 | 15.80 |
| Comparison[1] | 6.64 | 85.82 | + | — |
| Comparison[2] | 0.79 | 3.63 | 13.27 | 20.22 |

[1] Compound according to Example 15 of German Patent 2,606,026
[2] Compound according to Example 4 of German Auslegeschrift 2,933,732
+ The whole substance volatilized at 290° C.

EXAMPLE 8

A mixture, prepared in a high-speed laboratory mixer, of:
- 100 parts by weight of polypropylene (® Hostalen PPK 1060 of Hoechst AG, melt index MFI 190/5 = 2.0/10 minutes, determined as specified in DIN 53,535),
- 0.2 part by weight of calcium stearate,
- 0.1 part by weight of pentaerythrityl tetrakis-3-(3,5-di-tert.-butyl-4-hydroxyphenyl)-propionate and
- 0.3 part by weight of the stabilizer to be tested, is converted into granules. The material stabilized in this manner is then melted in a laboratory extruder under the customary processing conditions and is spun into monofilaments via a spinning pump having an eight-orifice spinning nozzle. These filaments are then subsequently stretched in a 1:3 ratio and are texturized to give yarn of 40 dtex, which is processed to give test fabrics.

The samples of fabric are mounted on a perforated frame in such a way that a free aperture of diameter approx. 15.5 mm remains. The test specimens are artificially weathered in this form by irradiation with alternating light in a Xenotest X-1200 apparatus made by Original Hanau Quarzlampen GmbH. The intensity of the radiation was modulated by UV filter (special filter glass, d = 1.7 mm). The stability to light was tested as specified in DIN 53,387 (17 minutes dry period, 3 minutes sprinkling, black panel temperature 45° C., relative atmospheric humidity during the dry period 70 to 75%). At specific intervals of time, the fabrics are subjected to load, at the center, with a weight of diameter 6 mm and a pressure of 0.1 N/m². The time when the weight breaks through is taken as the end point of the test.

| Stabilizer according to Example | Exposure time in hours |
|---|---|
| 1 | 600 |
| 5 | 800+ |
| 6 | 800+ |
| No stabilizer | 280 |
| Comparison[1] | 500 |
| Comparison[2] | 800 |

+ not yet broken through
[1,2] comparison substances as in Example 7

I claim:

1. A polyalkyldiazaspirodecane derivative of the formula (I)

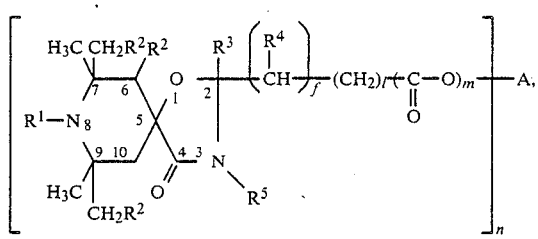

in which $R^1$ is hydrogen, oxygen, $C_1$ to $C_{12}$ alkyl which can be substituted by OH, or 2,3-dihydroxypropyl, $R^2$ represents hydrogen or $C_1$ to $C_5$ alkyl, $R^3$ represents $C_1$ to $C_5$ alkyl which can be substituted by —COOH, —COOCH$_3$ or —COOC$_2$H$_5$, or represents phenyl and $R^4$ is then hydrogen, or $R^3$ and $R^4$, together with the carbon atoms linking them, form a $C_5$ to $C_{12}$ cycloalkane ring, f is 0 or 1, l denotes an integer from 0 to 10, m is 1, n denotes 1, $R^5$ represents hydrogen, or $C_1$ to $C_{12}$ alkyl which can be substituted by OH in the 2-position, or represents a group of the formula —(CH$_2$)$_k$COOR$^6$ in which k is 1 or 2 and $R^6$ is a $C_1$ to $C_{18}$ alkyl group, A represents hydrogen, $C_1$ to $C_{18}$ alkyl, $C_3$ to $C_7$ alkenyl, $C_7$ to $C_9$ phenylalkyl, $C_5$ to $C_{12}$ cycloalkyl or 2,2,6,6-tetramethyl-4-piperidinyl.

2. A compound according to claim 1, wherein A is hydrogen or $C_1$ to $C_{18}$ alkyl.

3. A compound according to claim 1 selected from the group consisting of ethyl 2,7,7,9,9-pentamethyl-1-oxa-3,8-diaza-4-oxo-spiro-[4,5]-decan-2-ylacetate;

ethyl 2,7,7,9,9-pentamethyl-1-oxa-3,8-diaza-4-oxo-spiro-[4,5]-decan-2-ylpropionate; and methyl 2,7,7,9,9-pentamethyl-1-oxa-3,8-diaza-4-oxo-spiro-[4,5]-decan-2-ylbutane carboxylate.

* * * * *